US010188265B2

(12) United States Patent
Okamoto

(10) Patent No.: US 10,188,265 B2
(45) Date of Patent: Jan. 29, 2019

(54) FLEXIBLE INSERTION APPARATUS WITH INPUT DEVICE HAVING ACTUATOR FORCE CONTROL

(71) Applicant: OLYMPUS CORPORATION, Tokyo (JP)

(72) Inventor: Yasuhiro Okamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/974,610

(22) Filed: Dec. 18, 2015

(65) Prior Publication Data

US 2016/0100742 A1    Apr. 14, 2016

Related U.S. Application Data

(63) Continuation of application No. PCT/JP2014/065874, filed on Jun. 16, 2014.

(30) Foreign Application Priority Data

Jun. 18, 2013 (JP) .................................. 2013-127351

(51) Int. Cl.
A61B 1/00 (2006.01)
A61B 1/008 (2006.01)
(Continued)

(52) U.S. Cl.
CPC ........ *A61B 1/00006* (2013.01); *A61B 1/0002* (2013.01); *A61B 1/0016* (2013.01);
(Continued)

(58) Field of Classification Search
CPC ........... A61B 5/06; A61B 5/061–5/068; A61B 19/5244; A61B 2019/5246;
(Continued)

(56) References Cited

U.S. PATENT DOCUMENTS

2005/0245789 A1* 11/2005 Smith ................ A61B 1/00059
600/159
2007/0112255 A1* 5/2007 Ikeda .................. A61B 1/00039
600/146
(Continued)

FOREIGN PATENT DOCUMENTS

JP    H04-263830 A    9/1992
JP    H04-295326 A    10/1992
(Continued)

OTHER PUBLICATIONS

English translation of International Preliminary Report on Patentability dated Dec. 30, 2015 together with the Written Opinion received in related International Application No. PCT/JP2014/065874.
(Continued)

*Primary Examiner* — John P Leubecker
*Assistant Examiner* — William Chou
(74) *Attorney, Agent, or Firm* — Scully, Scott, Murphy & Presser, P.C.

(57) ABSTRACT

An insertion apparatus includes an elongated inserting section having a curving section, an input section which is provided in an operating section, receives an arbitrary input to curve the curving section in a movable range including a first range that includes the neutral input position and a second range that has an operation amount from the neutral input position exceeding the first range, a first actuator, a detecting section, a second actuator which gives a force towards the neutral position to the input section, and a control section which operates the first actuator and the second actuator, when the input amount to the input section is in the second range, thereby giving a force to the input section so that an input amount to the input section is in the first range.

9 Claims, 9 Drawing Sheets

(51) Int. Cl.
*A61B 1/005* (2006.01)
*A61B 1/05* (2006.01)
*G02B 23/24* (2006.01)

(52) U.S. Cl.
CPC .......... *A61B 1/0052* (2013.01); *A61B 1/0055* (2013.01); *G02B 23/2476* (2013.01); *A61B 1/005* (2013.01); *A61B 1/008* (2013.01); *A61B 1/0053* (2013.01); *A61B 1/0057* (2013.01); *A61B 1/05* (2013.01)

(58) Field of Classification Search
CPC .... A61B 2019/5248; A61B 2019/5251; A61B 2019/5261; A61B 1/005; A61B 1/0051; A61B 1/0052; A61B 1/0055; A61B 1/0057; A61B 1/00147; A61B 1/00006
USPC .................. 600/109, 139–152, 160; 606/108
See application file for complete search history.

(56) References Cited

U.S. PATENT DOCUMENTS

| | | | | |
|---|---|---|---|---|
| 2007/0161861 A1* | 7/2007 | Kawai | ................ | A61B 1/00055 600/145 |
| 2008/0221592 A1* | 9/2008 | Kawai | ................ | A61B 1/0055 606/130 |
| 2009/0149711 A1* | 6/2009 | Tanaka | ................ | A61B 1/0052 600/152 |
| 2010/0161129 A1* | 6/2010 | Costa | .................... | B25J 9/1697 700/259 |
| 2011/0234780 A1* | 9/2011 | Ito | .......................... | A61B 34/20 348/65 |
| 2011/0282154 A1* | 11/2011 | Umemoto | ........... | A61B 1/0051 600/152 |
| 2013/0312563 A1* | 11/2013 | Kawashima | ............ | B25J 18/02 74/490.01 |
| 2015/0157191 A1* | 6/2015 | Phee | ...................... | B25J 9/1674 600/106 |

FOREIGN PATENT DOCUMENTS

| | | |
|---|---|---|
| JP | H06-169883 A | 6/1994 |
| JP | 2003-230535 A | 8/2003 |
| JP | 2011-019550 A | 2/2011 |
| WO | WO 2012/074013 A1 | 6/2012 |

OTHER PUBLICATIONS

International Search Report dated Aug. 12, 2014 issued in PCT/JP2014/065874.

* cited by examiner

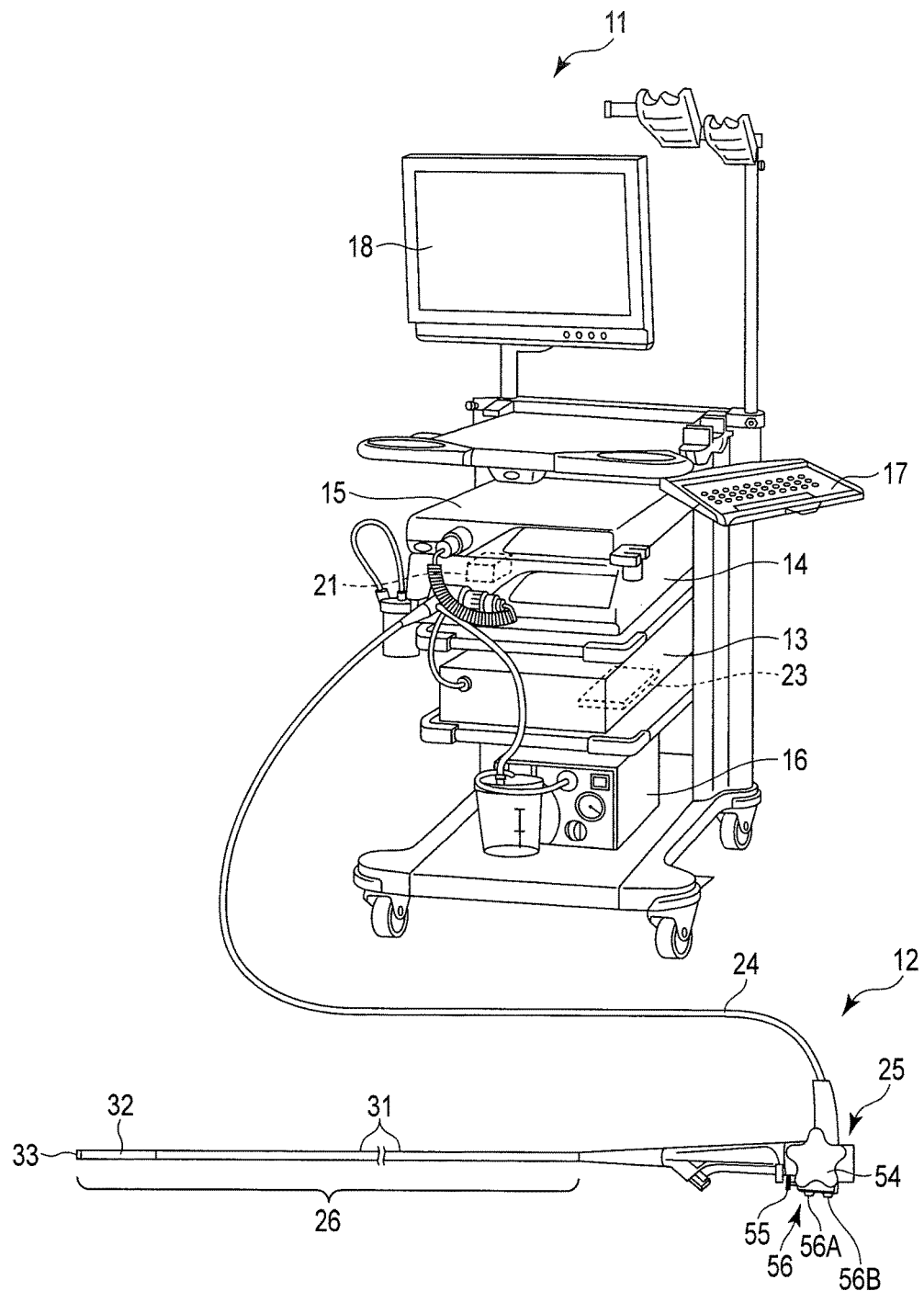
F I G. 1

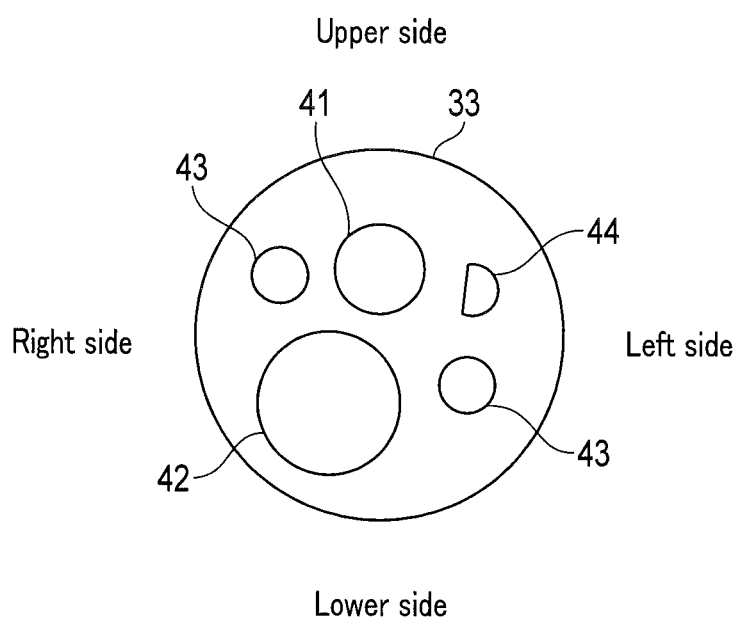
F I G. 2

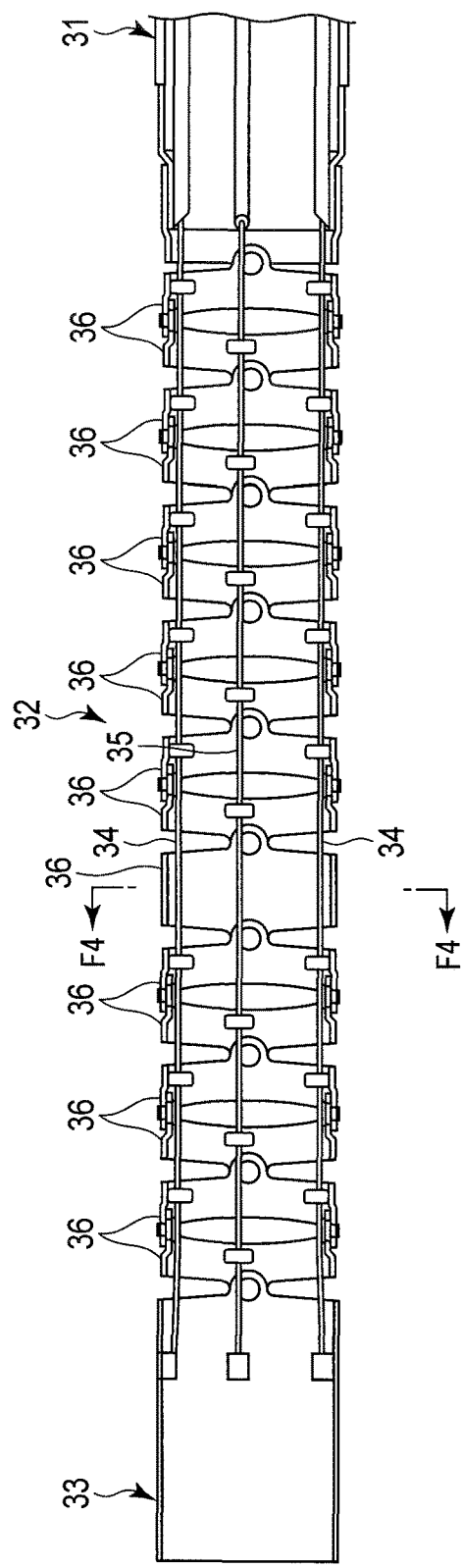
F I G. 3

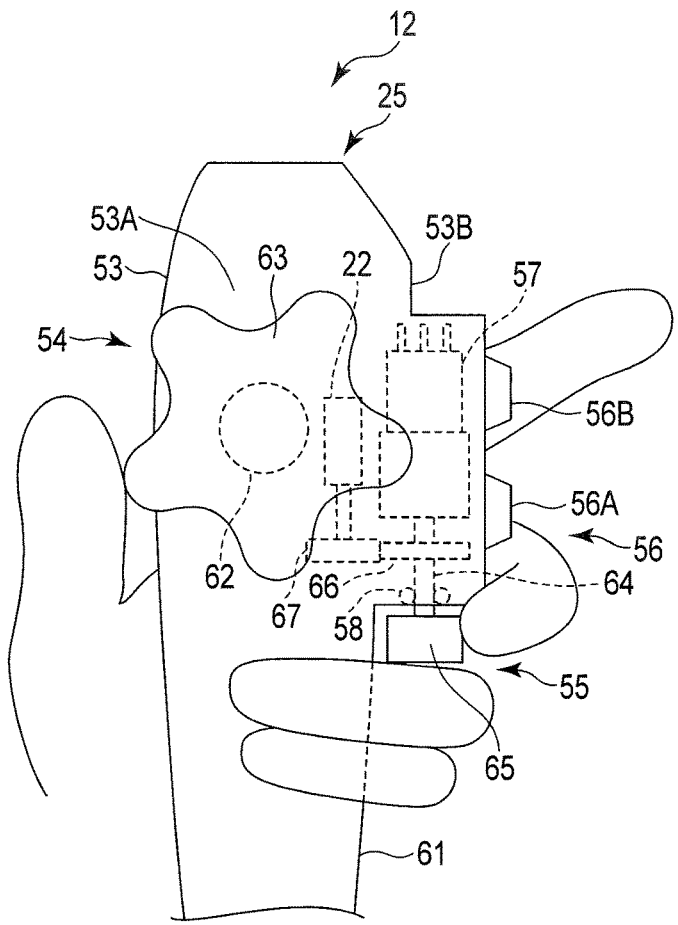
F I G. 7
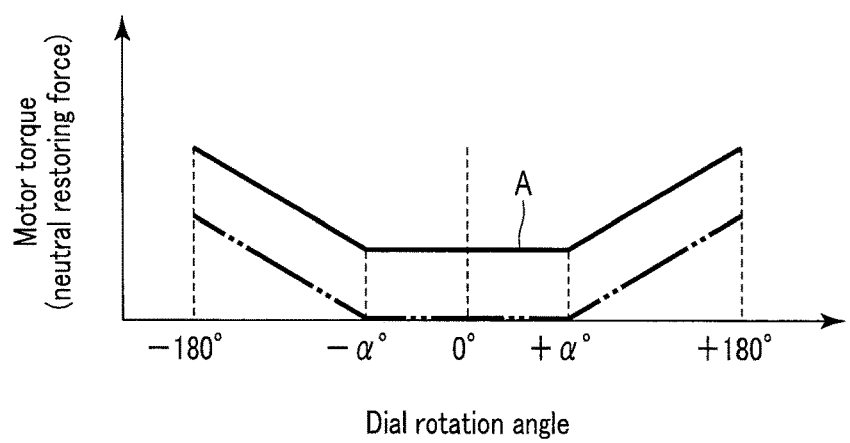
F I G. 8

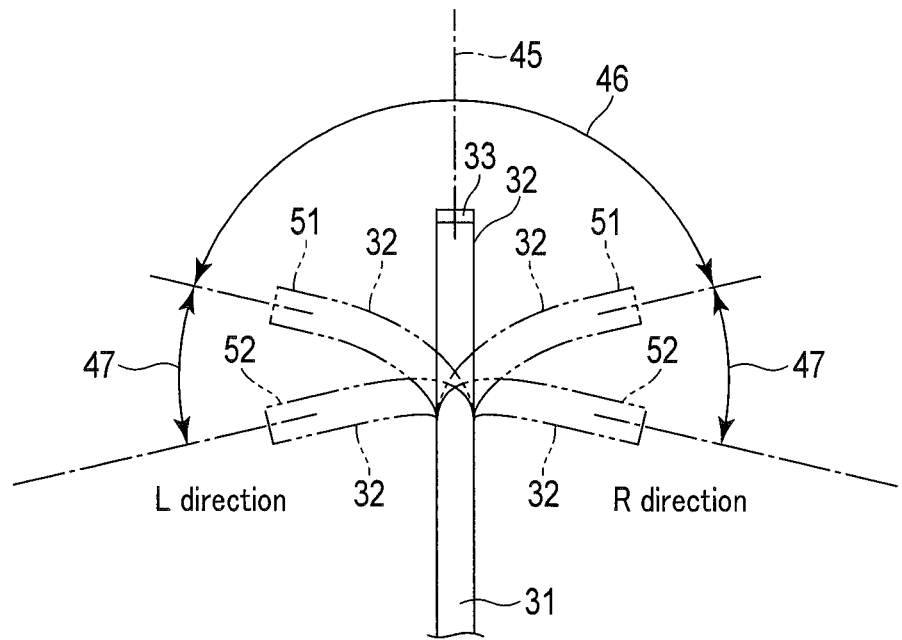
F I G. 9
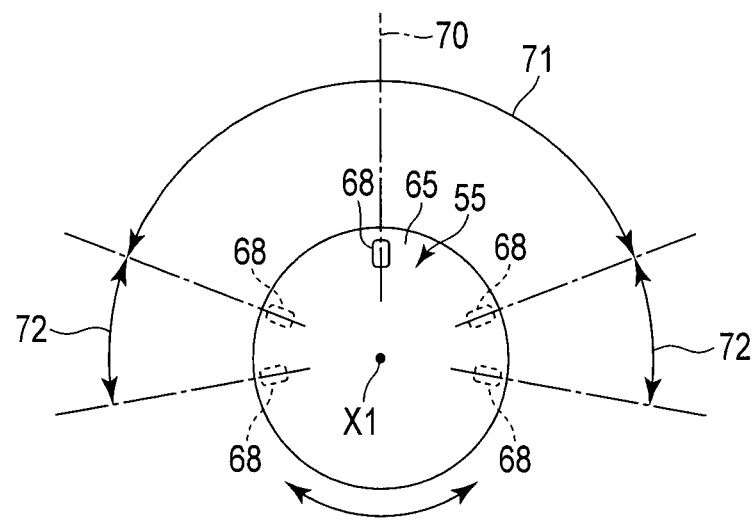
F I G. 10

FLEXIBLE INSERTION APPARATUS WITH INPUT DEVICE HAVING ACTUATOR FORCE CONTROL

CROSS-REFERENCE TO RELATED APPLICATIONS

This application is a Continuation Application of PCT Application No. PCT/JP2014/065874, filed Jun. 16, 2014 and based upon and claims the benefit of priority from Japanese Patent Application No. 2013-127351, filed Jun. 18, 2013, the entire contents of which are incorporated herein by reference.

TECHNICAL FIELD

The present invention relates to an insertion apparatus that is inserted into a cavity.

BACKGROUND ART

In general, an insertion apparatus like an endoscope for a cavity has a flexible inserting section that is inserted into a sample to, for example, observe or treat a lesioned part in the sample, and an operating section which performs an operation to curve this inserting section in a UD direction and an RL direction. The operating section has a UD angle knob to perform an operation in the UD direction, and an RL angle knob to perform an operation in the RL direction. In the case of, e.g., observing or treating a lesioned part, the inserting section can be curved in the UD direction and the RL direction by operating the UD angle knob and the RL angle knob.

Further, among endoscopes, there is one that drives curving of a curving section in the UD direction and the RL direction by a motor.

For example, in an endoscope in International Publication No. 2012-074013, an inserting section can be curved in an up-and-down (UD) direction by a manual operation, and it can be curved in a left-and-right (RL) direction automatically by driving of a motor. An operating section has a knob for operations in the up-and-down (UD) direction and a dial for operations in the left-and-right (RL) direction.

For example, in Jpn. Pat. Appln. KOKAI Publication No. H6-169883, an endoscope has a motor to curve a curving portion, a device to drive a motor in accordance with an operation amount, and a joystick to operate the device. In this endoscope, when fingers of a user are released from the joystick, the motor is driven to curve the curving section in a center direction, i.e., to decrease a curving angle.

SUMMARY OF INVENTION

For example, in an insertion apparatus like an endoscope in Jpn. Pat. Appln. KOKAI Publication No. H6-169883, when a curving section is curved by driving of a motor and then fingers of a user are released from a joystick, a curving angle is controlled to approximately 0° irrespective of a state of the curving angle of the curving section. Thus, there is a case that the inserting apparatus exhibits a behavior which makes it all the more difficult for the user to use, depending on the use state.

It is an object of the present invention to provide an insertion apparatus having improved convenience.

Solution to Problem

An insertion apparatus comprises, an elongated inserting section having a curving section which has a neutral position and is curvable at an arbitrary angle and which is arranged near a distal end section, an input section which is provided in an operating section arranged on a proximal end side of the inserting section, has a neutral input position corresponding to an input to hold the curving section at the neutral position, and receives an arbitrary input to curve the curving section in a movable range including a first range that includes the neutral input position and a second range that has an operation amount from the neutral input position exceeding the first range, a first actuator which is operated to curve the curving section at a certain curving angle;

a detecting section which detects an input to the input section, a second actuator which gives a force towards the neutral input position to the input section, and a control section which operates the first actuator to curve the curving section at a curving angle corresponding to an input amount to the input section, and operates the second actuator, when the input amount to the input section corresponds to the second range, thereby giving a force to the input section so that an input amount to the input section is in the first range.

Additional objects and advantages of the invention will be set forth in the description which follows, and in part will be obvious from the description, or may be leaned by practice of the invention. The objects and advantages of the invention may be realized and obtained by means of the instrumentalities and combinations particularly pointed out hereinafter.

BRIEF DESCRIPTION OF DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a perspective view showing an overall configuration of an endoscope apparatus according to a first embodiment;

FIG. 2 is a front view showing a distal end hard section of the endoscope apparatus depicted in FIG. 1 from an end face side;

FIG. 3 is a cross-sectional view showing curving pieces, first wires, and second wires provided in a curving section of the endoscope apparatus depicted in FIG. 1;

FIG. 7 is a schematic view showing a state that the operating section of the endoscope apparatus depicted in FIG. 6 is gripped with a left hand;

FIG. 8 is a graph showing conditions of a rotation angle of a second dial section and a value of current allowed to flow through the second actuator in a program stored in a control device of the endoscope apparatus according to each of the first embodiment and a first modification;

FIG. 9 is a schematic view showing a first range and a second range of a movable range of the curving section of the endoscope apparatus depicted in FIG. 7;

FIG. 10 is a plan view showing a second dial unit of the endoscope apparatus depicted in FIG. 6 from a direction of a rotation axis X1;

DESCRIPTION OF EMBODIMENTS

First Embodiment

Figure 4:
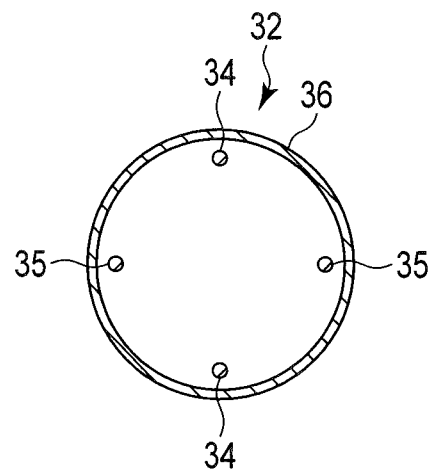
FIG. 4 is a cross-sectional view taken along a line F4-F4 depicted in FIG. 3.

FIG. 1 shows an overall structural view of an endoscope apparatus 11 as an example of an insertion apparatus according to the present invention. The endoscope apparatus 11 has an endoscope 12, a control device 13, a light source device 14, an image processing device 15, an air supply/water supply/suction device 16, a keyboard 17, a monitor 18, a first actuator 21, and a second actuator 22 (see FIG. 6).

The light source device 14 supplies light to an illumination lens 43 provided in a later-described distal end hard section 33 of the endoscope 12 under control of the control device 13. The air supply/water supply/suction device 16 supplies air/supplies water to a nozzle 44 provided in the distal end hard section 33 of the endoscope 12, or sucks a liquid, a tissue, or the like from a living body through a treatment tool insertion channel 42 under control of the control device 13. The image processing device 15 performs image processing to an image of a sample acquired through an objective lens 41 in the distal end hard section 33 of the endoscope 12, and displays it in the monitor 18 under control of the control device 13.

As shown in FIG. 1, the control device 13 is an example of a control section, and it is connected to a rotation detecting sensor 57 (see FIG. 6) incorporated in an operating section 25. The endoscope 12 detects a rotating direction and a rotation amount of a second dial section 65, i.e., an input by the rotation detecting sensor 57, and transmits a detection signal to the control device 13. The control device 13 operates the first actuator 21 in accordance with the rotating direction and the rotation amount detected by the rotation detecting sensor 57, and curves a curving section 32 in an R direction and an L direction. The control device 13 is also connected to the second actuator 22. The details of the control device 13 will be described later.

The first actuator 21 can give a driving force to curve the later-described curving section 32 of the endoscope 12 in the R direction (a RIGHT side) and the L direction (a LEFT side) shown in FIG. 2 and FIG. 9 in a movable range. The first actuator 21 is formed of, e.g., a motor such as a servo motor.

Figure 6:
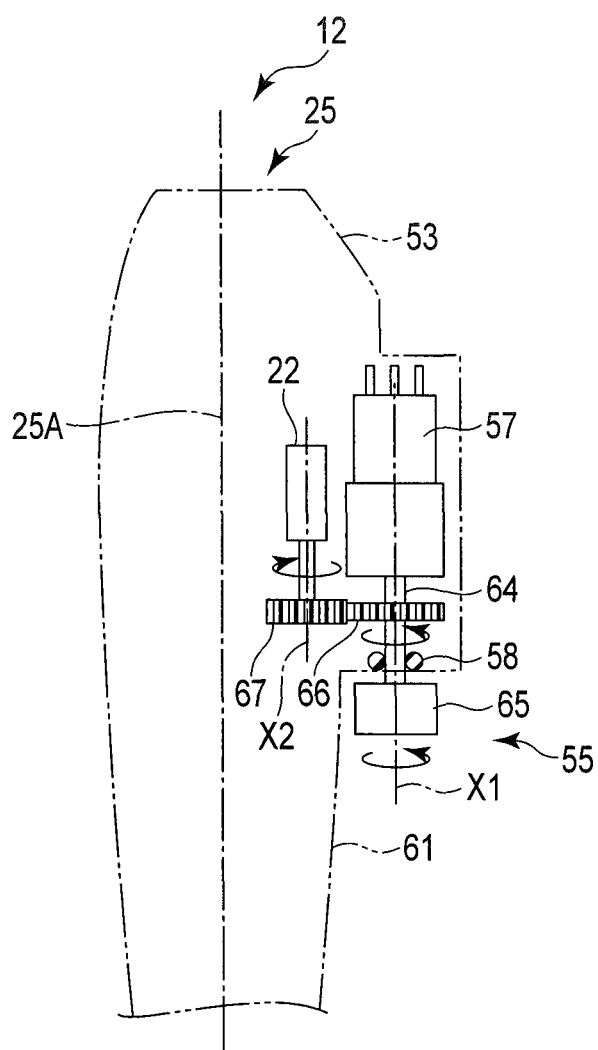
FIG. 6 is a schematic view showing the operating section of the endoscope apparatus depicted in FIG. 5, and a rotation detecting sensor and a second actuator provided therein.

As shown in FIG. 6, the second actuator 22 is supported in, e.g., a case 53 of the later-described operating section 25. The second actuator 22 can give a torque to the second dial section 65 through a gear section 66 under control of the control device 13. The second actuator 22 is formed of, e.g., a motor such as a servo motor.

As shown in FIG. 1, the endoscope 12 has a universal cord 24, the operating section 25, and an inserting section 26 that is inserted into a cavity (a sample).

The endoscope 12 is connected to the control device 13, the light source device 14, the image processing device 15, and the air supply/water supply/suction device 16 through the universal cord 24. A shaft having flexibility (not shown) is inserted into the universal cord 24. Driving force of the first actuator 21 is transmitted to a pair of second wires 35 (see FIG. 3 and FIG. 4) that are wound around a pulley and configured to curve the curving section 32 in the R direction and the L direction through the shaft having the flexibility, gears and the pulley (a second pulley) provided in the operating section 25.

Figure 5:
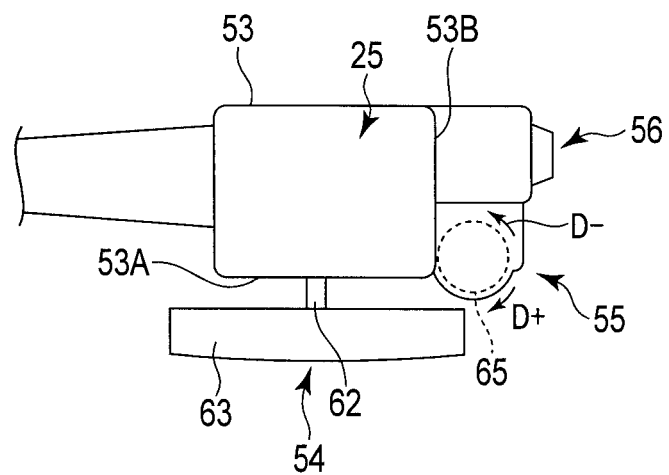
FIG. 5 is a schematic view showing an operating section from a direction opposite to a direction along which the curving section of the endoscope apparatus depicted in FIG. 1 is present, i.e., a proximal end side of the operating section.

As shown in FIG. 5 and FIG. 6, the operating section 25 has a case 53 made of, e.g., a synthetic resin material to have an inner space, a first dial unit 54 (a first curving operation unit) provided on a first wall portion 53A of the case 53, a second dial unit 55 (a second curving operation unit) provided near a second wall portion 53B of the case 53, a button section 56 provided near the second wall portion 53B of the case 53, the rotation detecting sensor (a detecting section) 57 provided in the case 53, and an O-ring 58 provided around a second shaft section 64 of the second dial unit 55. Each of the first wall portion 53A and the second wall portion 53B may be a planar surface or a curved surfaced. When each of the first wall portion 53A and the second wall portion 53B is the curved surface, it is preferable to form each portion so that it outwardly bulges to a longitudinal axis 25A of the operating section 25.

The case 35 has a support section 61. The support section 61 is placed at a position closer to the curving section 32 than the first wall portion 53A and the second wall portion 53B, and it can be supported by a fourth finger and a fifth finger of a left hand when a physician holds the operating section 25 with his/her left hand (see FIG. 7). When the operating section 25 is supported with the left hand, a fingertip of the fourth finger and a fingertip of the fifth finger are placed to be closer to a wrist than a fingertip of an index finger or a fingertip of a middle finger, which is a natural state hardly imposing a burden on the hand. Thus, a region of the support section 61 supported by the fourth finger and the fifth finger is formed with a shorter circumferential length around the longitudinal axis 25A than a region formed of the first wall portion 53A and the second wall portion 53B of the case.

As shown in FIG. 5, the first wall portion 53A is adjacent to the second wall portion 53B. As shown in FIG. 6 and FIG. 7, the O-ring 58 is interposed between the second shaft section 64 and the case 53, and maintains the inside of the case 53 in a water-tight state. Furthermore, the 0-ring 58 gives a certain rotational resistance (resistance force) to the second shaft section 64.

The rotation detecting sensor 57 is an example of a detecting section, and can detect a rotating direction (an input direction) and a rotation amount (an input amount) input to the second dial unit 55 (an input section), i.e., inputs. The rotation detecting sensor 57 is constituted of, e.g., a potentiometer, but any other kind of sensor (e.g., a rotary encoder) may be adopted as long as it can detect a rotating direction and a rotation amount of the second shaft section 64. The rotation detecting sensor 57 reads a rotation angle of the second dial section 65 through the second shaft section 64 of the second dial unit 55, and detects a rotating direction and a rotation amount of the second dial unit 55.

As shown in FIG. 7, the button section 56 has a first button 56A (an air supply/water supply, AW) that realizes air supply/water supply to the distal end hard section 33 of the endoscope through the nozzle 44, and a second button 56B (a suction button, S) that realizes suction at the distal end hard section 33 of the endoscope 12 through the nozzle 44.

The first dial unit 54 is a so-called UD angle knob that is operated at the time of curving the curving section 32 in the U direction and the D direction, i.e., two directions.

As shown in FIG. 7, the first dial unit 54 has a first shaft section 62 rotatably provided on the first wall portion 53A, a first dial section 63 fixed on one end portion of the first shaft section 62, and a first pulley (not shown) which is provided in the case 53 and fixed on the other end portion of the first shaft section 62. The first dial section 63 has a substantially star-like shape and has, e.g., five claws. The later-described first wires 34 configured to curve the curving section 32 in the U direction and the D direction are wound around the first pulley.

Thus, when a user rotates the first dial unit 54 around a center axis thereof, the later-described curving section 32 is curved in the U direction or the D direction through the first pulley and the first wires 34 in accordance with a rotating direction and a rotation amount of the unit. That is, in the endoscope apparatus 11 according to this embodiment, along the U direction and the U direction, a mechanism that curves the curving section 32 by electrical driving of a motor or the like is not provided. However, like the later-described R direction and L direction, the first actuator 21 such as a motor may be provided so that the curving section 32 can be curved in the U direction and the D direction by electrical driving.

The second dial unit 55 is a so-called RL angle knob that is operated at the time of curving the curving section 32 in the R direction and the L direction, i.e., two directions.

As shown in FIG. 6 and FIG. 7, the second dial unit 55 has the second shaft section 64 which is provided on the second wall portion 53B side and rotatable to the case 53, the second dial section 65 (a second knob) fixed on one end portion of the second shaft section 64, indexes 68 that are provided on the second dial section 65 and configured to indicate rotation angles of the second dial unit 55, and a gear section 66 which is provided on the second shaft section 64 and to which a rotation force from the gear section 67 of the second actuator 22 is transmitted. The second dial unit 55 is an example of an input section configured to operate the first actuator 21. The second dial section 65 has a columnar shape. A peripheral surface of the second dial section 65 is knurled, for example. The second dial section 65 is provided on the curving section 32 side of a center axis (the first shaft section 62) of the first dial section 63 in the longitudinal axis 25A of the operating section 25. The other end portion of the second shaft section 64 is connected to the rotation detecting sensor (the detecting section) 57 in the case 53.

In the second dial unit 55, the second shaft section 64 and the second dial section 65 can rotate around the rotation axis X1. As shown in FIG. 10, the second dial unit 55 has a neutral input position 70 corresponding to an input to hold the later-described curving section 32 at a neutral position 45. The second dial unit 55 can rotate in a movable range including a first range 71 including the neutral input position 70 and a second range 72 having an operation amount from the neutral input position 70 exceeding the first range 71.

It is to be noted that, in FIG. 6, the rotation axis X1 of the second shaft section 64, the second dial section 65, and the gear section 66 and a rotation axis X2 of the second actuator 22 and the gear section 67 are drawn parallel. However, a relationship between the rotation axes X1 and X2 is not restricted thereto as long as a driving force of the second actuator 22 can be transmitted to the second dial section 65 by, for example, selecting the gear sections 66 and 67.

When a user rotates the second dial section 65 of the second dial unit 55, the rotation detecting sensor 57 detects a rotating direction and a rotation amount thereof. The first actuator 21 is driven in accordance with the rotating direction and the rotation amount detected by the rotation detecting sensor 57. Therefore, the curving section 32 is electrically driven to curve in the R direction and the L direction by the driving force of the first actuator 21 in accordance with the rotating direction and the rotation amount of the second dial section 65 of the second dial unit 55.

It is to be noted that, in this embodiment, the description is given as to the example where the curving section 32 is electrically driven to curve in the R direction and the L direction, but the curving section may be manually curved in the R direction and the L direction like said curving mechanism that curves the curving section 32 in the U direction and the D direction. In this case, the curving section 32 is electrically driven to curve in the U direction and the D direction by the driving force of the first actuator 21. The curving section 32 may be electrically driven to curve in not only the R direction and the L direction, but it may be also electrically driven to curve in the U direction and the D direction.

As shown in FIG. 1, the inserting section 26 includes an elongated soft section 31 having flexibility, the curving section 32 provided at a distal end of this soft section 31, and the distal end hard section 33 provided at a distal end of this curving section 32. As shown in FIG. 3 and FIG. 4, the pair of first wires 34 configured to curve the curving section 32 in the U direction and the D direction and the pair of second wires 35 configured to curve the curving section 32 in the R direction and the L direction are inserted in the soft section 31 and the curving section 32. The curving section 32 has curving pieces 36 aligned in a longitudinal direction of the inserting section 26.

As shown in FIG. 2, an objective lens 41, the treatment tool insertion channel 42 through which a treatment tool such as a forceps can be protruded from the distal end of the inserting section 26 or a liquid, a tissue, or the like in a cavity of a sample can be sucked, the illumination lenses 43, the nozzle 44 from which water or air that cleans a distal end face of the distal end hard section 33 can be discharged are provided in the distal end hard section 33.

As shown in FIG. 9, the curving section 32 can curve in the R direction and the L direction at an arbitrary angle in a turning range including a first curving range 46 including the neutral position 45 (e.g., ±0°) and a second curving range 47 placed outside the first curving range 46.

The first curving range 46 corresponds to the first range 71 which is a rotation angle in the range of ±α° or less of the second dial section 65 (see FIG. 8). That is, as shown in FIG. 5 and FIG. 9, when the second dial section 64 is rotated α° in the clockwise direction (a positive direction D+) as seen from the proximal end side of the operating section 25, the curving section 32 curves α° to the neutral position 45 in the R direction. At this time, the curving section 32 is placed on an outer boundary of the first curving range 46, and a position will be called a first curved state 51 on an R side.

Likewise, when the second dial section 65 is rotated α° in the counterclockwise direction (a negative direction D−) as seen from the proximal end side of the operating section 25, the curving section 32 curves α° to the neutral position 45 in the L direction. At this time, likewise, the curving section 32 is placed on an outer boundary of the first curving range 46 (a boundary on the opposite side of the boundary in the R direction), and this position will be called a first curved state 51 on an L side. It is to be noted that, as a value of α, a physician or the like can set a desired value in the range of 5 to 180 to the control device 13 using, e.g., the keyboard 17. Thus, it can be said that the first curving range 46 is the range from the neutral position 45 to the first curved state 51.

It is to be noted that, in this embodiment, a maximum curving angle of the curving section 32 is described as ±180° to the neutral position 45.

Further, when the second dial section 65 is rotated 180° (namely, +180°) in the clockwise direction as seen from the proximal end side of the operating section 25, the curving section 32 enters a second curved state 52 on the R side that it is curved the most in the R direction. At this time, the second curved state 52 on the R side is a so-called maximum curved state of the curving section 32. Likewise, when the second dial section 65 is rotated 180° (namely, −180°) in the counterclockwise direction as seen from the proximal end side of the operating section 25, the curving section 32 enters a second curved state 52 on the L side (a maximum curved state) that the curving section 32 is curved the most in the L direction. That is, it can be said that the second curving range 47 is the range that the curving section 32 changes to the second curved state 52 from the first curved state 51.

In addition, it is preferable to form the curving section 32 so that a rotating direction and a rotation amount of the second dial section 65, i.e., rotation inputs to the second dial section 65 correspond to a curving angle of the curving section 32. Thus, when the second dial section 65 is rotated, e.g., 30° from the neutral position (0°) in the clockwise direction as seen from the proximal end side of the operating section 25, the curving section 32 curves at the curving angle of 30° in the R direction from the neutral position 45 (0°). Likewise, the curving angle of the curving section 32 becomes 90° in the R direction when the second dial section 65 is rotated, e.g., 90° in the clockwise direction as seen from the proximal end side of the operating section 25, and the curving angle of the curving section 32 becomes 180° in the R direction when the second dial section 65 is rotated, e.g., 180° in the clockwise direction as seen from the proximal end side of the operating section 25. Furthermore, when the second dial section 65 is rotated, e.g., 30° in the counterclockwise direction as seen from the proximal end side of the operating section 25, the curving section 32 curves at the curving angle of 30° in the L direction from the neutral position (0°). Likewise, the curving angle of the curving section 32 becomes 90° in the L direction when the second dial section 65 is rotated, e.g., 90° in the counterclockwise direction as seen from the proximal end side of the operating section 25, and the curving angle of the curving section 32 becomes 180° in the L direction when the second dial section 65 is rotated, e.g., 180° in the counterclockwise direction as seen from the proximal end side of the operating section 25. It is to be noted that, in this embodiment, the rotation angle of the second dial section 65 is equal to the curving angle of the curving section 32, but the rotation angle of the second dial section 65 and the curving angle of the curving section 32 may have a proportional relation. Specifically, the rotation angle of the second dial section 65 may be set to be larger than the curving angle of the curving section 32 by using a multiple rotation type sensor as the rotation detecting sensor 57.

The first curving range 46, i.e., the range of ±α° from the neutral position 45 is a range that is frequently used in a normal use mode (a normal use range). In the first curving range 46, a physician who is a user often performs visual recognition or a biopsy of the inside of a cavity or conducts processing or inspections by inserting a treatment tool or an inspection tool into the treatment tool insertion channel 42. Thus, in this embodiment, the first curving range 46 can be used as an engage region where the curving section 32 that is curved at a certain angle temporarily holds this angle without change. It is to be noted that the engage state is canceled when a user performs different input to the second dial section 65 as will be described later. Furthermore, although the curving of the curving section 32 in the R direction and the L direction is described here, the same configuration can be applied to the curving in the U direction and the D direction when the curving section 32 is electrically driven to curve in the U direction and the D direction as described above.

As shown in FIG. 1, the control device 13 is an example of the control section, and it is connected to the rotation detecting sensor 57. The rotation detecting sensor 57 detects a rotating direction and a rotation amount of the second dial section 65, and transmits a detection signal to the control device 13. The control device 13 operates the first actuator 21 in accordance with the rotation amount of the second dial section 65 detected by the rotation detecting sensor 57, and curves the curving section 32 at a curving angle according to the rotation amount in the R direction and the L direction. The control device 13 is also connected to the second actuator 22.

As shown in FIG. 1, the control device 13 has a hard disk drive device 23 which is an example of a memory section. The hard disk drive device 23 stores a program which sets a torque applied to the second actuator 22 for the rotating direction and the rotation amount (a dial rotation angle) detected by the rotation detecting sensor 57. With this program, an electric current is allowed to flow to the second actuator 22 from a power supply circuit of the control device 13 under conditions indicated by a solid line in such a graph as shown in FIG. 8. That is, the hard disk drive device 23 stores the conditions of the value of current allowed to flow through the second actuator 22 via the program in accordance with inputs to the second dial section 65.

When a detection value from the rotation detecting sensor 57 at the time of input to the second dial section 65 (an input section) corresponds to the second curving range 47 (see FIG. 9) in the movable range of the curving section 32, the control device 13 gives a rotational force to the second dial section 65 in a direction opposite to an input direction by the second actuator 22 based on the program. That is, when an input amount to the second dial section 65 (the input section) corresponds to the second curving range 47 (the second range 72), the control device 13 gives the rotational force to the second dial section 65 through the second actuator 22 in a direction to return the second dial section 65 to a position corresponding to the first curving range 46 (see FIG. 9) in accordance with the program.

As shown in FIG. 8, as a rotation angle of the second dial section 65 increases in a region where the rotation angle of the second dial section 65 is +α° (α is a certain value which is larger than 5 and smaller than 180, and more preferably a certain value which is 60 or more and 120 or less (e.g., 90)) and more, the control device 13 raises a value of current allowed to flow through the second actuator 22 based on the program. It is to be noted that the positive direction D1 described herein means the clockwise direction seen from the proximal end side of the operating section 25, and the negative direction D2 means the counterclockwise direction seen from the proximal end side of the operating section 25 (see FIG. 5). Under control of the program, as the rotation angle of the second dial section 65 increases in the region where the rotation angle of the second dial section 65 is +α° or more, torque generated by the second actuator 22 (torque in the counterclockwise direction seen from the proximal end side of the operating section 25) increases.

Likewise, as the rotation angle of the second dial section 65 increases in the region where the rotation angle of the second dial section 65 is −α° or less, the program raises the value of current allowed to flow through the second actuator 22. Consequently, as the rotation angle of the second dial section 65 increases in the region where the rotation angle of the second dial section 65 is −α° or less, torque generated by the second actuator 22 (torque in the clockwise direction seen from the proximal end side of the operating section 25) increases. It is to be noted that, in this embodiment, the value of current allowed to flow through the second actuator 22 (a motor) and the torque generated by the second actuator 22 have a proportional relation.

An operation of the endoscope apparatus 11 and the control executed by the control device 13 according to this embodiment will now be described.

A physician who is a user grips the operating section 25 with, for example, his/her left hand.

The universal cord 24 is placed at a position between a thumb and an index finger of his/her left hand, a ball of the thumb is arranged on a claw of the first dial section 63, and the support section 61 is supported by a fourth finger and a fifth finger. Moreover, a ball of the index finger of the left hand is arranged on a position where a first button 56A (an air supply/water supply button) or a second button 56B (a suction button) can be operated, and a ball of a middle finger is arranged on the second dial section 65. In this manner, the physician holds the operating section 25 in his/her left hand to wrap it, holds the inserting section 26 in his/her right hand, and inserts it into a cavity from a distal end toward a proximal end of the inserting section 26, thereby performing a desired inspection or treatment.

When the physician wants to curve the curving section 32 in either the U direction or the D direction, as shown in FIG. 7, the first dial section 63 is rotated in the clockwise direction or the counterclockwise direction by, e.g., the ball of the thumb. Consequently, the first pulley fixed to the first shaft section 62 is rotated in the operating section 25, and one of the pair of first wires 34 wound around the first pulley is pulled toward the proximal end side of the operating section 25, and the curving section 32 curves in one of the U direction and the D direction. Specifically, the curving section curves in the D (down) direction when the first dial section in FIG. 7 is rotated in the clockwise direction, and the curving section curves in the U (up) direction when the same is rotated in the counterclockwise direction.

On the other hand, when the physician wants to curve the curving section 32 in either the R direction or the L direction, as shown in FIG. 7, the second dial section 65 is rotated in the positive direction D+ or the negative direction D− by, e.g., the ball of the middle finger of the left hand. The curving section curves in the R (right) direction when the second dial section 65 is rotated in the positive direction D+, and the curving section 32 curves in the L (left) direction when the same is rotated in the negative direction D−.

Specifically, a rotating direction and a rotation amount of the second dial section 65 are read by the rotation detecting sensor 57. The rotation detecting sensor 57 transmits an electrical signal corresponding to the rotating direction and the rotation amount of the second dial section 65 to the control device 13. The control device 13 operates the first actuator 21, and the first actuator 21 transmits torque (rotational force) to the pair of second wires 35 through the shaft having flexibility, the gears, and the second pulley. One of the second wires 35 is pulled toward the proximal end side of the operating section 25, and the curving section 32 curves in either the R direction or the L direction. It is to be noted that the rotation detecting sensor 57 does not obstruct rotation of the second dial section 65, and the rotation of the second dial section 65 does not require a large force.

When an input amount input to the second dial section 65 corresponds to the first curving range 46 (the first range 71), as shown in FIG. 8, a small current is allowed to flow through the second actuator 22 to generate a fixed torque, and a position of the second dial unit 55 is maintained as it is. Thus, for example, when the curving section 32 curves in the R direction or the L direction from the neutral position 45 shown in FIG. 9, the second dial section 65 must be rotated against the torque of the second actuator 22. However, the torque given to the second actuator 22 is smaller than the force input to the second dial section 65, and hence the rotation (the input) of the second dial section 65 does not require a large force.

When the input amount input to the second dial section 65 corresponds to the first curving range 46 (the first range 71), the control device 13 keeps giving a fixed torque to the second actuator 22 in accordance with the program after curving of the curving section 32 to a certain angle is completed, namely, after the physician stops the input to the second dial section 65. Thus, the second dial section 65 is prevented from rotating on its own. Therefore, when the input amount input to the second dial section 65 corresponds to the first curving range 46 (the first range 71), the control device 13 drives the second actuator 22, and generates a holding torque so that the curving section 32 holds the certain angle as it is (see a solid line part A in FIG. 8).

On the other hand, when the input amount input to the second dial section 65 corresponds to the second curving range 47 (the second range 72), as shown in FIG. 8, as the input amount to the second dial section 65 increases, gradually increasing torque (restoring force to the neutral position 45) is given to the second actuator 22. Although the torque given to the second actuator 22 is smaller than the force input to the second dial section 65, the rotation (the input) of the second dial section 65 requires the gradually increasing force as the input amount to the second dial section 65 increases.

When the input amount input to the second dial section 65 corresponds to the second curving range 47 (the second range 72), the control device 13 gives a rotational force to restore the input amount of the second dial section 65 corresponding to the first curving range 46, namely, in a direction opposite to an input direction by the second actuator 22 in accordance with the program after the curving of the curving section 32 to a certain angle in the second curving range 47 is completed, i.e., after the physician stops the input to the second dial section 65. Specifically, when the input amount to the second dial section 65 is +α° or more and +180° or less (i.e., in the second curving range 47 (the second range 72) on the R side), the torque is given to return the second dial section 65 to a rotation angle of +α°.

It is to be noted that the force given to the second dial section 65 by the second actuator 22 in this manner is smaller than the force input to the second dial section 65 by the finger. Consequently, when the physician releases his/her finger from the second dial section 65, the curving section 32 is automatically returned to the first curved state 51 on the R side.

Additionally, in this embodiment, when the physician releases his/her finger from the second dial section 65, the curving section 32 returns to the first curved state 1 on the R side, but the control effected by the control device 13 is not restricted thereto. The control device 13 may perform control so that the curving section 32 can return to the neutral position 45 or the first curving range 46 on the L side beyond the neutral position 45 when the physician releases his/her finger from the second dial section 65.

Likewise, when the input amount to the second dial section 65 is −α° or more and −180° or less (i.e., in the second curving range 47 (the second range 72) on the L side), torque is given to return the second dial section 65 to the rotation angle of −α°. It is to be noted that the force given to the second dial section 65 by the second actuator 22 in this manner is smaller than the force input to the second dial section 65 by the finger. Consequently, when the physician releases his/her finger from the second dial section 65, the curving section 32 is automatically returned to the first curved state 51 on the L side.

Further, the control device 13 may perform control so that the curving section 32 can return to the neutral position 45 or the first curving range 46 on the R side beyond the neutral position 45 on the L side when the physician releases his/her finger from the second dial section 65.

According to the first embodiment, the endoscope apparatus 11 includes the inserting section 26 having the curving section 32 which has the neutral position 45 and can curve at an arbitrary angle, the input section to which an arbitrary input to curve the curving section 32 in the movable range is input, the movable range having the neutral input position 70 corresponding to an input to hold the curving section 32 at the neutral position 45 and including the first range 71 which includes the neutral input position 70 and the second range 72 where an operation amount from the neutral input position 70 exceeds the first range 71, the first actuator 21 which is operated to curve the curving section 32 at a certain curving angle, the detecting section which detects an input to the input section, the second actuator 22 which gives a force to the input section, and the control section which operates the first actuator 21 to curve the curving section 32 at a curving angle corresponding to an input amount to the input section, operates the second actuator 22 when the input amount to the input section corresponds to the second range 72, and gives a force to the input section so that the input amount to the input section can fall within the first range 71.

A conventional endoscope apparatus that manually curves a curving section has properties that an angle of the curving section 32 that is curved at a particularly small curving angle is held (namely, engaged) as it is at a position where a restoring elastic force of an outer shell portion (an angle tube) made of rubber surrounding the curving section 32 and a sliding friction force of the first wires 34 and the second wires 35 incorporated in the curving section 32 are balanced. According to this configuration, in the second curving range 47, torque can be given to the input section (the second dial section 65) by the second actuator 22 to return to the first curving range 46. Consequently, the same operational feeling as that of the conventional manual endoscope apparatus can be provided. That is, in the first curving range 46, a curving angle of the curving section 32 can be maintained as it is, and a target region of a sample can be, e.g., inspected or treated while the physician temporarily fixes a position (positioning) of the curving section 32.

According to this embodiment, the control device 13 has the memory section, and the memory section stores a control signal that is supplied to the second actuator 22 in accordance with an input to the input section. According to this configuration, since the memory section (the hard disk drive device 23) stores such a control signal, it is possible to appropriately perform control to return a curving angle to the first curving range 46 when the curving angle of the curving section 32 is in the second curving range 47.

The value of current is set so that a force given to the input section from the second actuator 22 increases as an input to the input section increases when the input to the input section corresponds to the second curving range 47 (the second range 72). According to this configuration, when the physician releases his/her hand from the input section (the second dial section 65), the force can be applied to slowly return the input section to a position corresponding to the first curving range 46 (the first range 71) when an input amount to the input section is relatively small in the second curving range 47 (the second range 72), or it can be applied to rapidly return the same when the input amount to the input section is relatively large in the second curving range 47 (the second range 72). Consequently, the same operational feeling as that of the conventional manual endoscope apparatus 11 can be provided.

The force given to the input section by the second actuator 22 is smaller than the force input to the input section, namely, the force to operate the input section by the finger. According to this configuration, as to the curving section 32 in the second curving range 47, when the physician releases his/her hand from the input section, the curving section 32 can be returned to the first curving range 46. Consequently, when the physician is observing a sample in the second curving range 47, the curving range 32 can be prevented from unexpectedly returning to the first curving range 46. Further, fatigue of the fingers of the physician can be alleviated. Furthermore, since a curving angle on a boundary between the first range and the second range can be set by the control device 13, convenience for the physician can be further improved.

It is to be noted that, in the first embodiment, when the second dial section 65 (the input section) is present at a position corresponding to the first curving range (the first range 71), a holding torque is generated by the second actuator 22. As a modification (a first modification), this holding torque may be prevented from being generated at a position corresponding to the first curving range 46 (the first range 71). At this time, the control device 13 (the control section) outputs to a built-in power supply circuit a signal to set the value of current which is allowed to flow through the second actuator 22 to zero. In this case, a rotational resistance force provided by sliding friction of the O-ring 58, frictional force of the gear section 66, and rotational resistance force of the second shaft section 64 connected to the rotation detecting sensor 57 are set to be relatively high, and the second dial section 65 is set to hardly rotate, whereby the curving section 32 can be held (engaged) without its angle changing. In the case of this modification, a relationship between a rotation angle of the second dial section 65 (the input section) and the torque of the second actuator 22 is such a relationship as indicated by an alternate long and two short dashes line in FIG. 8. That is, the control device 13 stores a program to drive the second actuator 22 (allow a current to flow through the second actuator 22) under conditions indicated by the alternate long and two short dashes line in such a graph as shown in FIG. 8.

Second Embodiment

Figure 11:
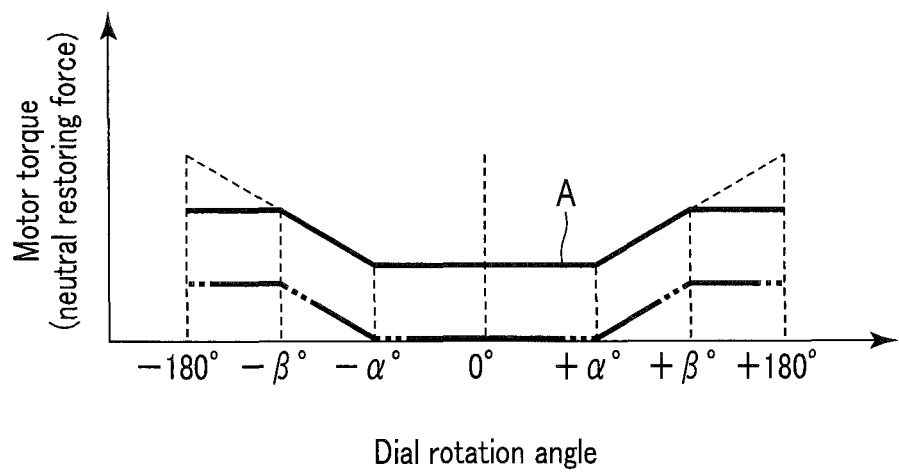
FIG. 11 is a graph showing conditions of a rotation angle of a second dial section and a value of current allowed to flow through a second actuator in a program stored in a control device of an endoscope apparatus according to each of a second embodiment and a second modification.

An endoscope apparatus 11 according to a second embodiment will now be described with reference to FIG. 11. In the endoscope apparatus 11 according to the second embodiment, a program stored in a control device 13 is different from that in the first embodiment, but other parts are the same as those in the first embodiment. Thus, a part different from the first embodiment will be mainly described, and illustration or a description of parts equal to those in the first embodiment will be omitted. That is, this embodiment is a modification of the first embodiment.

The control device 13 has a hard disk drive device 23 which is an example of a memory section. The hard disk drive device 23 stores a program to drive a second actuator, namely, allow a current to flow through the second actuator 22 under conditions indicated by a solid line in such a graph as shown in FIG. 11. According to the program, when an input amount to a second dial section 65 (an input section) corresponds to a second curving range 47 (a second range 72), rotational force is given to the second dial section 65 through the second actuator 22 in a direction (a direction to approximate 0°) opposite to an input direction.

According to the program of this embodiment, in a region where a rotation angle of the second dial section 65 is $+\alpha°$ or more and $+\beta°$ ($\beta$ is a certain value larger than $\alpha$ and smaller than 180, or more preferably a certain value which is 120 or more and 150 or less, for example) or less, as the rotation angle of the second dial section 65 increases, a value of current allowed to flow through the second actuator 22 is raised. Consequently, in the region where the rotation angle of the second dial section 65 is $+\alpha°$ or more and $+\beta°$ or less, as the rotation angle of the second dial section 65 increases, torque generated by the second actuator 22 (torque in the counterclockwise direction as seen from a proximal end side of an operating section 25) increases.

Further, according to the program of this embodiment, in a region where the rotation angle of the second dial section 65 is $+\beta°$ or more and 180° or less, even when the rotation angle of the second dial section 65 increases, a value of current allowed to flow through the second actuator 22 is fixed. Consequently, in the region where the rotation angle of the second dial section 65 is $+\beta°$ or more and 180° or less, even when the rotation angle of the second dial section 65 increases, torque generated by the second actuator 22 (torque in the counterclockwise direction as seen from the proximal end side of the operating section 25) is fixed.

Likewise, according to the program, in a region where the rotation angle of the second dial section 65 is $-\alpha°$ or more and $-\beta°$ or less, as the rotation angle of the second dial section 65 increases, a value of current allowed to flow through the second actuator 22 is raised. Consequently, in the region where the rotation angle of the second dial section 65 is $-\alpha°$ or more and $-\beta°$ or less, as the rotation angle of the second dial section 65 increases, the torque generated by the second actuator 22 (the torque in the clockwise direction seen from the proximal end side of the operating section 25) increases.

Furthermore, according to the program of this embodiment, in a region where the rotation angle of the second dial section 65 is $-\beta°$ or more and $-180°$ or less, even when the rotation angle of the second dial section 65 increases, a value of current allowed to flow through the second actuator 22 is fixed. Consequently, in the region where the rotation angle of the second dial section 65 is $-\beta°$ or more and $-180°$ or less, even when the rotation angle of the second dial section 65 increases, the torque generated by the second actuator 22 (the torque in the clockwise direction seen from the proximal end side of the operating section 25) is fixed.

According to this embodiment, the value of current is set so that, when an input amount to an input section (the second dial section 65) corresponds to a second curving range 47 (a second range 72), the force given to the input section by the second actuator 22 increases as the input to the input section increases, and the force given to the input section by the second actuator 22 becomes fixed when the input to the input section becomes larger than a certain value ($\pm\beta°$).

According to this configuration, when the input amount (the rotation angle) to the input section (the second dial section 65) increases, an operation force amount to operate the input section does not become excessively large. Consequently, when a physician holds the input section (the second dial section 65) at a position corresponding to the second curving range 47 (the second range 72), his/her holding finger can be prevented from becoming tired.

It is to be noted that, in the second embodiment, when the second dial section 65 (the input section) is present at a position corresponding to a first curving range 46 (a first range 71), the holding torque (torque that maintains the curving section 32 in a curved state as it is) is generated in the second actuator 22. As a modification (a second modification), this holding torque may be prevented from being generated at a position corresponding to the first curving range 46 (the first range 71). At this time, the control device 13 outputs to a power supply circuit a signal to set the value of current which is to flow through the second actuator 22 to zero. In this case, a rotational resistance force provided by sliding friction of an O-ring 58, frictional force of a gear section 66, and rotational resistance force of a second shaft section 64 connected to a rotation detecting sensor 57 are set to be relatively high, and the second dial section 65 is set to hardly rotate, whereby the curving section 32 can be held (engaged) without its angle changing. In the case of this modification (the second modification), a relationship between a rotation angle of the second dial section 65 (the input section) and the torque of the second actuator 22 is such a relationship as indicated by an alternate long and two short dashes line in FIG. 11. That is, the control device 13 stores a program to drive the second actuator 22 (allow a current to flow through the second actuator 22) under conditions indicated by the alternate long and two short dashes line in such a graph as shown in FIG. 11.

Third Embodiment

Figure 12:
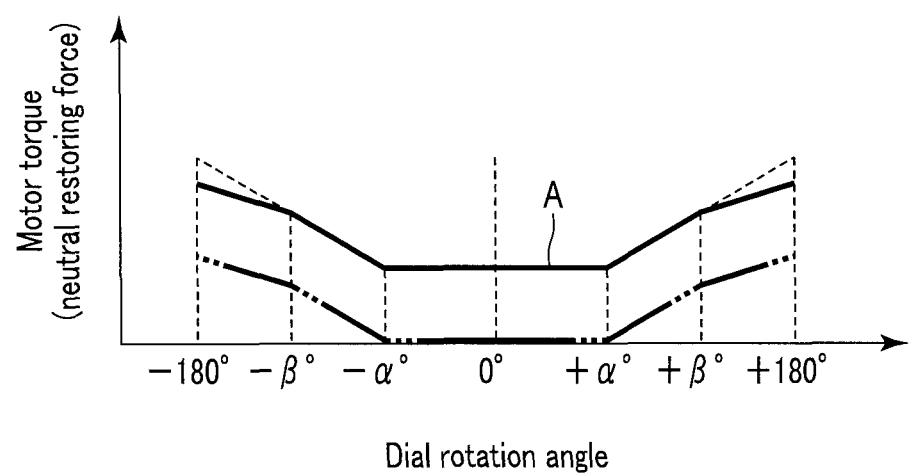
FIG. 12 is a graph showing conditions of a rotation angle of a second dial section and a value of current allowed to flow through a second actuator in a program stored in a control device of an endoscope apparatus according to each of a third embodiment and a third modification.

An endoscope apparatus 11 according to a third embodiment will now be described with reference to FIG. 12. In the endoscope apparatus 11 according to the third embodiment, a program stored in a control device 13 is different from that in the second embodiment, but other parts are the same as those in the second embodiment. Thus, a part different from the second embodiment will be mainly described, and illustration or a description of parts equal to those in the second embodiment will be omitted. That is, this embodiment is a modification of the first embodiment and the second embodiment.

The control device 13 has a hard disk drive device 23 which is an example of a memory section. The hard disk drive device 23 stores a program to drive a second actuator 22 (allow a current to flow through the second actuator 22) under conditions indicated by a solid line in such a graph as shown in FIG. 12. According to the program, when an input amount to a second dial section (an input section) corresponds to a second curving range 47 (a second range 72), rotational force is given to the second dial section 65 (the input device) through the second actuator 22 in a direction opposite to an input direction.

According to the program of this embodiment, in a region where a rotation angle of the second dial section 65 is +α° or more and +β° or less, as the rotation angle of the second dial section 65 increases, a value of current allowed to flow through the second actuator 22 is raised at a first increasing rate. Thus, in the region where the rotation angle of the second dial section 65 is +α° or more and +β or less, as the rotation angle of the second dial section 65 increases, the torque generated by the second actuator 22 (the torque in the counterclockwise direction seen from a proximal end side of an operating section 25) increases at the first increasing rate.

Moreover, according to the program of this embodiment, in a region where the rotation angle of the second dial section 65 is +β° or more and 180° or less, when the rotation angle of the second dial section 65 increases, a value of current allowed to flow through the second actuator 22 is increased at a second increasing rate smaller than the first increasing rate. Consequently, in the region where the rotation angle of the second dial section 65 is 4° or more and 180° or less, when the rotation angle of the second dial section 65 increases, the torque generated by the second actuator 22 (the torque in the counterclockwise direction seen from the proximal end side of the operating section 25) increases at the second increasing rate.

Likewise, according to the program, in a region where the rotation angle of the second dial section 65 is −α° or more and −β° or less, as the rotation angle of the second dial section 65 increases, a value of current allowed to flow through the second actuator 22 is raised at the first increasing rate. Consequently, in the region where the rotation angle of the second dial section 65 is −α° or more and −β° or less, as the rotation angle of the second dial section 65 increases, the torque generated by the second actuator 22 (the torque in the clockwise direction seen from the proximal end side of the operating section 25) increases at the first increasing rate.

Furthermore, according to the program of this embodiment, in a region where the rotation angle of the second dial section 65 is −β° or more and −180° or less, when the rotation angle of the second dial section 65 increases, a value of current allowed to flow through the second actuator 22 is raised at the second increasing rate smaller than the first increasing rate. Consequently, in the region where the rotation angle of the second dial section 65 is −β° or more and −180° or less, when the rotation angle of the second dial section 65 increases, the torque generated by the second actuator 22 (the torque in the clockwise direction seen from the proximal end side of the operating section 25) is raised at the second increasing rate.

According to this embodiment, the value of current is set so that, when an input to an input section (the second dial section 65) corresponds to a second curving range 47 (a second range 72), the force given to the input section by the second actuator 22 increases at a certain increasing rate (the first increasing rate) as the input to the input section increases, and the increasing rate (the second increasing rate) of the force given to the input section by the second actuator 22 becomes smaller than the certain increasing rate when the input amount to the input section becomes larger than a certain value (±β°).

According to this configuration, when the input amount to the input section (the second dial section 65) becomes the certain value or more, the increasing rate of the force given to the input section can be reduced to be smaller than the certain increasing rate (the increasing rate when the input amount to the input section is smaller than the certain value, the first increasing rate). Consequently, like the second embodiment, even when the input amount (the rotation angle) to the input section increases in a region corresponding to the second curving range 47 (the second range 72), an operation force amount required to operate the input section can be prevented from becoming extremely large. Further, when the input amount to the input section becomes the certain value or more, since a resistance force applied at the time of rotating the input section gradually increases, a physician can grasp a curving amount of the curving section 32 to some extent with the sense of his/her fingers.

It is to be noted that, in the third embodiment, when the second dial section 65 (the input section) is present at a position corresponding to a first curving range 46, a holding torque (torque that maintains the curving section 32 in a curved state without change) is generated by the second actuator 22. As a modification (a third modification), this holding torque may be prevented from being generated at a position corresponding to the first curving range 46 (the first range 71). At this time, the control device 13 outputs to a power supply circuit a signal to set the value of current allowed to flow through the second actuator 22 to zero. In this case, a rotational resistance force provided by sliding friction of an O-ring 58, frictional force of a gear section 66, and rotational resistance force of a second shaft section 64 connected to a rotation detecting sensor 57 are set to be relatively high, and the second dial section 65 is set to hardly rotate, whereby the curving section 32 can be held (engaged) without changing its angle. In the case of this modification (the third modification), a relationship between a rotation angle of the second dial section 65 (the input section) and the torque of the second actuator 22 is such a relationship as indicated by an alternate long and two short dashes line in FIG. 12, for example. That is, the control device 13 stores a program to drive the second actuator 22 (allow a current to flow through the second actuator 22) under conditions indicated by the alternate long and two short dashes line in such a graph as shown in FIG. 12.

Fourth Embodiment

Figure 13:
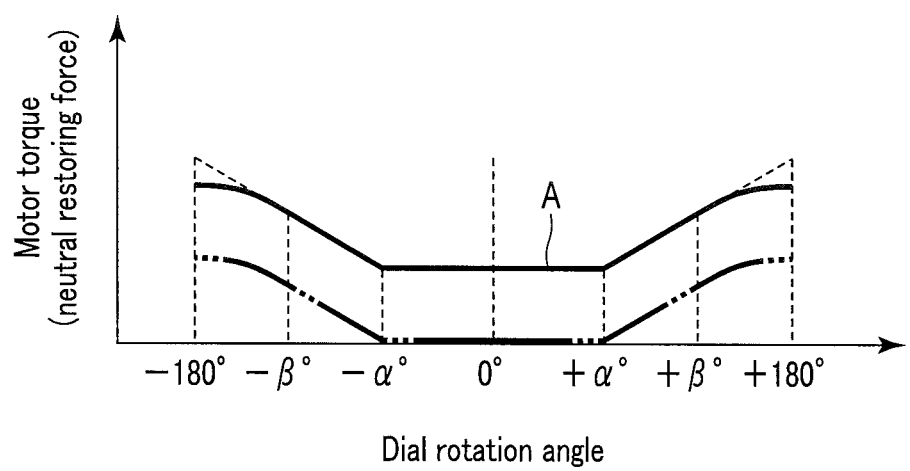
FIG. 13 is a graph showing conditions of a rotation angle of a second dial section and a value of current allowed to flow through a second actuator in a program stored in a control device of an endoscope apparatus according to each of a fourth embodiment and a fourth modification.

An endoscope apparatus 11 according to a fourth embodiment will now be described with reference to FIG. 13. In the endoscope apparatus 11 according to the fourth embodiment, a program stored in a control device 13 is different from that in the third embodiment, but other parts are the same as those in the third embodiment. Thus, a part different from the third embodiment will be mainly described, and illustration or a description of parts equal to those in the third embodiment will be omitted. That is, this embodiment is a modification of the first embodiment and the third embodiment.

The control device 13 has a hard disk drive device 23 which is an example of a memory section. The hard disk drive device 23 stores a program to drive a second actuator 22 (allow a current to flow through the second actuator 22) under conditions indicated by a solid line in such a graph as shown in FIG. 13. According to the program, when an input amount to a second dial section 65 (an input section) corresponds to a second curving range 47 (a second range 72), a rotational force is given to the second dial section 65 through the second actuator 22 in a direction opposite to an input direction.

According to the program of this embodiment, in a region where a rotation angle of the second dial section 65 is +α° or more and +β° or less, as the rotation angle of the second dial section 65 increases, a value of current allowed to flow through the second actuator 22 is raised at a certain increasing rate. Thus, in the region where the rotation angle of the second dial section 65 is +α° or more and +β° or less, as the rotation angle of the second dial section 65 increases, torque generated by the second actuator 22 (torque in the counterclockwise direction seen from a proximal end side of an operating section 25) increases.

Moreover, according to the program of this embodiment, in a region where the rotation angle of the second dial section 65 is +β° or more and 180° or less, when the rotation angle of the second dial section 65 increases, a value of current flowing through the second actuator 22 rises, but an increasing rate of the value of current is gradually reduced. Consequently, in the region where the rotation angle of the second dial section 65 is +β° or more and 180° or less, when the rotation angle of the second dial section 65 increases, torque generated by the second actuator 22 (torque in the counterclockwise direction seen from the proximal end side of the operating section 25) increases, but an increasing rate of the torque is gradually reduced.

Likewise, according to the program, in a region where the rotation angle of the second dial section 65 is −α° or more and −β° or less, as the rotation angle of the second dial section 65 increases, a value of current allowed to flow through the second actuator 22 is raised at a certain increasing rate. Consequently, in the region where the rotation angle of the second dial section 65 is −α° or more and −β° or less, as the rotation angle of the second dial section 65 increases, the torque generated by the second actuator 22 (torque in the clockwise direction seen from the proximal end side of the operating section 25) increases.

Furthermore, according to the program of this embodiment, in a region where the rotation angle of the second dial section 65 is −β° or more and −180° or less, when the rotation angle of the second dial section 65 increases, a value of current flowing through the second actuator 22 rises, but an increasing rate of the value of current is gradually reduced. Consequently, in the region where the rotation angle of the second dial section 65 is −β° or more and −180° or less, when the rotation angle of the second dial section 65 increases, the torque generated by the second actuator 22 (the torque in the clockwise direction seen from the proximal end side of the operating section 25) increases, but an increasing rate of the torque is gradually reduced.

According to this embodiment, the value of current is set so that, when an input amount to an input section (the second dial section 65) becomes higher than a certain value (±β°), the increasing rate of the force given to the input section by the second actuator 22 is reduced as the input amount to the input section further increases.

According to this configuration, when the input amount to the input section becomes a certain value or more, the increasing rate of the force given to the input section can be reduced to be smaller than a certain increasing rate (the increasing rate when the input amount to the input section is smaller than the certain value (±β°)). Consequently, like the second and third embodiments, even when the input amount (the rotation angle) to the input section (the second dial section 65) increases in a region corresponding to the second curving range 47, an operation force amount required to operate the input section can be prevented from becoming extremely large. Additionally, when the input amount to the input section becomes the certain value or more, since a resistance force applied at the time of rotating the input section gradually increases, a physician can grasp a curving amount of the curving section 32 to some extent with the sense of his/her fingers. Further, a change in increasing rate of the torque given to the input section (the second dial section 65) can be prevented from becoming drastic between the case where the input amount to the input section is the certain value or less and the case where the input amount to the input section is the certain value or more. Consequently, the physician can be prevented from developing a feeling of strangeness in the input to the input section between the case where the input amount to the input section is the certain value or less and the case where the same is the certain value or more.

It is to be noted that, in the fourth embodiment, when the second dial section 65 (the input section) is present at a position corresponding to a first curving range 46 (a first range 71), a holding torque (torque that maintains the curving section 32 in a curved state without change) is generated in the second actuator 22. As a modification (a fourth modification), this holding torque may be prevented from being generated at a position corresponding to the first curving range 46. At this time, the control device 13 outputs to a power supply circuit a signal to set the value of current allowed to flow through the second actuator 22 to zero. In this case, a rotational resistance force provided by sliding friction of an O-ring 58, frictional force of a gear section 66, and rotational resistance force of a second shaft section 64 connected to a rotation detecting sensor 57 are set to be relatively high, and the second dial section 65 is set to hardly rotate, whereby the curving section 32 can be held (engaged) without changing its angle. In the case of this modification (the fourth modification), a relationship between a rotation angle of the second dial section 65 (the input section) and the torque of the second actuator 22 is such a relationship as indicated by an alternate long and two short dashes line in FIG. 13. That is, the control device 13 stores a program to drive the second actuator 22 (allow a current to flow through the second actuator 22) under conditions indicated by the alternate long and two short dashes line in such a graph as shown in FIG. 13.

It is to be noted that the example using the endoscope 12 has been described in the foregoing embodiments including the modifications, but the illumination optical system (the light source device 14, the illumination lens 43, and others) and the observation optical system (the image processing device 15, the objective lens 41, and others) are not necessarily required. Thus, it is possible to use the foregoing embodiments including the modifications for an insertion apparatus such as a catheter including an inserting section which has an electrically-driven curvable curving section. It is not necessarily required to incorporate the illumination optical system and the observation optical system in such an insertion apparatus like the endoscope 12.

The present invention is not restricted to the foregoing embodiments, and it can be appropriately modified without departing from a gist of the invention. Further, the insertion apparatuses according to the respective embodiments can be combined to constitute one insertion apparatus.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

REFERENCE SINGS LIST

11 . . . endoscope apparatus (insertion apparatus), 12 . . . endoscope, 13 . . . control device, 21 . . . first actuator, 22 . . . second actuator, 23 . . . hard disk drive device, 32 . . . curving device, 45 . . . neutral position, 46 . . . first range, 47 . . . second range, 57 . . . rotation detecting sensor (detecting section), 58 . . . O-ring, 65 . . . second dial section (input section).

The invention claimed is:

1. An endoscope apparatus comprising:
   an elongated inserting section having a curving section which has a neutral position and is curvable at an arbitrary angle and which is arranged near a distal end section;
   an input device which is provided in an operating section arranged on a proximal end side of the elongated inserting section, has a neutral input position corresponding to an input to hold the curving section at the neutral position, and receives an arbitrary input to curve the curving section in a movable range including a first range that includes the neutral input position and a second range that has an operation amount from the neutral input position exceeding the first range, wherein the input device comprises:
   a shaft section;
   a dial section arranged on an end portion of the shaft section; and
   a first gear section arranged on the shaft section;
   a detecting sensor which detects a rotating direction and a rotation amount of the dial section which is an input to the input device;
   a first actuator which is operated to curve the curving section at a certain curving angle;
   a second actuator which gives a force towards the neutral input position to the input device; and
   a controller configured to operate the first actuator to curve the curving section at a curving angle corresponding to an input amount to the input device, operate the second actuator to move the input device towards the first range, when the input amount to the input device is in the second range, and stop a drive of the second actuator, when the input amount to the input device moves into the first range,
   the second actuator being arranged in the operating section,
   a second gear section of the second actuator transmitting a rotation force of the second actuator to the input device via the first gear section.

2. The endoscope apparatus according to claim 1, wherein the controller has a memory which stores the force given to the input device by the second actuator as a value of current in accordance with an input to the input device.

3. The endoscope apparatus according to claim 2, wherein the value of current is set so that the force given to the input device by the second actuator increases as the input to the input device increases, when the input to the input device is in the second range.

4. The endoscope apparatus according to claim 3, wherein the value of current is set so that the force given to the input device by the second actuator increases as the input to the input device increases, when the input to the input device is in the second range, and set so that the force given to the input device by the second actuator is constant, when the input to the input device is larger than a certain value.

5. The endoscope apparatus according to claim 3, wherein the value of current is set so that the force given to the input device by the second actuator increases at a certain increasing rate as the input amount to the input device increases, when the input to the input device is in the second range, and the increasing rate of the force given to the input device by the second actuator is set to be lower than the certain increasing rate, when the input amount to the input device is larger than a certain value.

6. The endoscope apparatus according to claim 5, wherein the value of current is set so that the increasing rate of the force given to the input device by the second actuator decreases as the input to the input device further increases, when the input to the input device is larger than the certain value.

7. The endoscope apparatus according to claim 1, wherein the force given to the input device by the second actuator is smaller than a force input to the input device.

8. The endoscope apparatus according to claim 1, wherein the second actuator gives a force in a direction opposite to an input direction to the input device.

9. The endoscope apparatus according to claim 1, wherein a curving angle of the elongated inserting section at a boundary between the first range and the second range is settable by the controller.

* * * * *